United States Patent
Rosenberg

(10) Patent No.: US 7,318,813 B2
(45) Date of Patent: Jan. 15, 2008

(54) SELF ADJUSTING HYDROCEPHALUS VALVE

(75) Inventor: Meir Rosenberg, Newton, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 441 days.

(21) Appl. No.: 10/607,121

(22) Filed: Jun. 26, 2003

(65) Prior Publication Data

US 2004/0267187 A1    Dec. 30, 2004

(51) Int. Cl.
*A61M 5/00* (2006.01)
(52) U.S. Cl. .............................. 604/9; 604/8; 604/264
(58) Field of Classification Search ............. 604/7–10, 604/6.16, 264; 251/157, 175; 137/81.1
See application file for complete search history.

(56) References Cited

U.S. PATENT DOCUMENTS

| | | | |
|---|---|---|---|
| 2,859,770 A | 11/1958 | Buivid | |
| 2,938,540 A | 5/1960 | Schatzman et al. | |
| 3,450,155 A | 6/1969 | Froehner et al. | |
| 3,886,948 A | 6/1975 | Hakim | |
| 3,977,391 A | 8/1976 | Fleischmann | |
| 3,999,553 A | 12/1976 | Spitz et al. | |
| 4,027,661 A | 6/1977 | Lyon et al. | |
| 4,106,510 A | 8/1978 | Hakim et al. | |
| 4,332,255 A | 6/1982 | Hakim et al. | |
| 4,387,715 A | 6/1983 | Hakim et al. | |
| 4,443,218 A | 4/1984 | DeCant, Jr. et al. | |
| 4,551,128 A | 11/1985 | Hakim et al. | |
| 4,595,390 A | 6/1986 | Hakim et al. | |
| 4,610,658 A * | 9/1986 | Buchwald et al. | 604/9 |
| 4,615,691 A | 10/1986 | Hakim et al. | |
| 4,627,443 A | 12/1986 | Chubbuck et al. | |
| 4,729,762 A | 3/1988 | Doumenis | |
| 4,772,257 A | 9/1988 | Hakim et al. | |
| 4,776,839 A | 10/1988 | Doumenis | |
| 4,787,886 A * | 11/1988 | Cosman | 604/9 |
| 4,867,741 A | 9/1989 | Portnoy | |
| 5,069,663 A | 12/1991 | Sussman et al. | |
| 5,535,740 A | 7/1996 | Baghaee-Rezaee et al. | |
| 5,810,761 A * | 9/1998 | Saens-Arrollo | 604/9 |
| 5,928,182 A | 7/1999 | Kraus et al. | |
| 5,931,186 A | 8/1999 | Skoglund | |
| 5,935,084 A * | 8/1999 | Southworth | 600/561 |
| 5,980,480 A | 11/1999 | Rubenstein et al. | |
| 6,264,625 B1 * | 7/2001 | Rubenstein et al. | 604/9 |
| 6,953,444 B2 * | 10/2005 | Rosenberg | 604/9 |

FOREIGN PATENT DOCUMENTS

EP    1 331 019    7/2003

OTHER PUBLICATIONS

EP Communication, from corresponding EP 04 253 832.2, dated Jan. 18, 2007.

* cited by examiner

*Primary Examiner*—Leslie R. Deak
(74) *Attorney, Agent, or Firm*—Nutter, McClennen & Fish, LLP

(57) ABSTRACT

A self adjusting hydrocephalus valve that continuously drains cerebrospinal fluid at a rate which is proportional to the average pressure difference across the valve. The valve employs a ball-in-cone mechanism having an associated biasing element that is insensitive to high frequency pressure variations for regulating the opening of the valve mechanism. The biasing element includes flexible bellows having a preset tension.

20 Claims, 4 Drawing Sheets

P = pressure
R = resistance

SELF ADJUSTING HYDROCEPHALUS VALVE

CROSS-REFERENCE TO RELATED APPLICATIONS

Not applicable.

STATEMENT REGARDING FEDERALLY SPONSORED RESEARCH

Not Applicable.

FIELD OF THE INVENTION

The invention relates generally to medical devices for directing bodily fluids from one region of a patient to another region. More specifically, this invention relates to shunt systems having a pressure controlled variable resistance valve. Even more specifically, this invention relates to a self adjusting hydrocephalus valve having damping features that provides a drainage rate that is proportional to the average pressure over time.

BACKGROUND OF THE INVENTION

Hydrocephalus is a condition afflicting patients who are unable to regulate cerebrospinal fluid flow through their body's own natural pathways. Produced by the ventricular system, cerebrospinal fluid (CSF) is normally absorbed by the body's venous system. In a patient suffering from hydrocephalus, the cerebrospinal fluid is not absorbed in this manner, but instead accumulates in the ventricles of the patient's brain. If left untreated, the increasing volume of fluid elevates the patient's intracranial pressure and can lead to serious medical conditions such as compression of the brain tissue and impaired blood flow to the brain.

The treatment of hydrocephalus has conventionally involved draining the excess fluid away from the ventricles and rerouting the cerebrospinal fluid to another area of the patient's body, such as the abdomen or vascular system. A drainage system, commonly referred to as a shunt, is often used to carry out the transfer of fluid. In order to install the shunt, typically a scalp incision is made and a small hole is drilled in the skull. A proximal, or ventricular, catheter is installed in the ventricular cavity of the patient's brain, while a distal, or drainage, catheter is installed in that portion of the patient's body where the excess fluid is to be reintroduced.

To regulate the flow of cerebrospinal fluid and maintain the proper pressure in the ventricles, a pump or one-way control valve can be placed between the proximal and distal catheters. Generally, the shunt systems include a valve mechanism that operates to permit fluid flow only once the fluid pressure reaches a certain threshold level. That is, fluid enters the valve only when the fluid pressure overcomes the valve mechanism's resistance to open. Some valve mechanisms permit the adjustment, or programming, of the opening pressure level, or resistance level, at which fluid flow commences. These valve mechanisms can comprise a variety of configurations. For example, the valve mechanism can be configured as a ball-in-cone as illustrated and described in U.S. Pat. Nos. 3,886,948, 4,332,255, 4,387,715, 4,551,128, 4,595,390, 4,615,691, 4,772,257, and 5,928,182, all of which are hereby incorporated by reference.

An essential goal of any hydrocephalus treatment and moreover of any hydrocephalus shunt system is to restore the balance between the formation and absorption of CSF in the patient. Research in this area has shown that, while the formation rate is insensitive to pressure, the absorption rate increases linearly with increasing pressure. Moreover, the formation and absorption rates vary significantly from patient to patient, with age and with the circadian cycle. Specifically, CSF formation rate increases with age starting from infancy to adulthood, but then continuously declines with age following adulthood. More importantly, the natural residual absorption rate in hydrocephalus patients varies from patient to patient. This patient-specific absorption rate determines the degree of shunt dependency for that particular patient. Due to these variations in CSF absorption and formation rates, it is nearly impossible to predict the necessary resistance level of the hydrocephalus valve that will lead to the restoration of normal physiologic pressures in the patient's brain ventricles.

Valve mechanisms that continuously drain CSF are well known, as are valve mechanisms that control and/or adjust the opening pressure and/or drainage rate of the patient's CSF. However, these valve mechanisms respond to the instantaneous fluid flow or pressure in the ventricles to achieve a predetermined pressure or flow rate. This artificially prescribed flow rate prevents normal physiologic pressure waveforms from occurring and it is suspected that the resulting unnatural pressure waveforms are responsible for the late development that is frequently seen in hydrocephalus. Current devices attempt to restore normal physiologic pressure waveforms by providing ways to adjust, or program, the opening pressure of the valve. However, these current devices still provide less than ideal results. There is thus a need for a simple valve device that will adjust its resistance to the patient's conditions, and which takes into account the variability of the absorption and formation rates of the patient over time.

SUMMARY OF THE INVENTION

The present invention provides a self adjusting hydrocephalus valve that continuously drains cerebrospinal fluid in a patient at a rate which is proportional to the average pressure difference across the valve over time. The valve employs a ball-in-cone mechanism having an associated resistor that is insensitive to high frequency pressure variations for regulating the opening of the valve mechanism. In an aspect of the present invention, the valve comprises a housing enclosing a chamber that is able to permit fluid flow therethrough. An inlet port in fluid communication with the chamber accommodates the passage of fluid into the chamber, while an outlet port in fluid communication with the chamber accommodates the passage of fluid out of the chamber.

To regulate the rate of fluid flow through the chamber, a valve mechanism is disposed within the housing. The valve mechanism includes a valve seat adjacent to an opening in the inlet port so that fluid can pass into the chamber. The valve mechanism also includes a blocking member configured to seat in the valve seat. When the blocking member is seated against the valve seat, CSF cannot enter through the valve seat and into the chamber. The valve mechanism also includes a biasing element (e.g., a spring, collapsible membrane, and/or flexible bellows) which communicates with the blocking member to bias the blocking member against the valve seat. The biasing element is configured to respond to a pressure difference within the valve, and has an adjustable resistance to allow fluid release at a rate which is proportional to an average pressure difference over time.

In one exemplary embodiment of the present invention, the biasing element is connected to the blocking member and acts on the blocking member like a resistor or a damper. The biasing element can comprise a spring element. Alternatively, or in addition, the biasing element can comprise at least one flexible bellows. The flexible bellows is defined by a base plate that communicates with the blocking member, an opposed end plate and a collapsible side wall extending between the plates. The plates can be round so that the flexible bellows has a generally cylindrical shape. On the end plate is an orifice to provide fluid communication between the flexible bellows and the chamber. The orifice, which allows fluid to pass into and out of the flexible bellows and into the chamber, can be round in shape. The flexible bellows can be formed from a biocompatible elastomeric material, including polymers (e.g., polyethylene, polyurethane), or metal (e.g., titanium, titanium alloy or titanium coated metal).

In another exemplary embodiment of the present invention, the biasing element comprises two flexible bellows. Each of the bellows can be cylindrically shaped. The first flexible bellows is similar in configuration to that described above, and is connected in parallel to a second, flexible bellows by an orifice which establishes a preset tension on the bellows. The orifice, which is located between the two bellows, allows fluid communication between the first and second bellows. In this embodiment, the biasing element is a closed fluidic system, and can be at least partially filled with a fluid such as air or an inert gas (e.g., argon). The first flexible bellows is connected to the blocking member. It is contemplated that the first and second flexible bellows are formed from an elastomeric material. For instance, each of the bellows can be formed from an elastomeric material, including polymers (e.g., polyethylene, polyurethane), or metal (e.g., titanium, titanium alloy or titanium coated metal).

In another aspect of the present invention, the blocking member is a spherical ball, while the valve seat has a contoured, spherical surface for mating with a portion of an outer surface of the spherical ball. The valve of the present invention can be housed within a shunt device for implantation inside a hydrocephalus patient.

Further features of the invention, its nature and various advantages, will be more apparent from the accompanying drawings and the following detailed description of the drawings and the preferred embodiments.

BRIEF DESCRIPTION OF THE DRAWINGS

The invention can be more fully understood from the following detailed description taken in conjunction with the accompanying drawings, in which.

DETAILED DESCRIPTION OF THE INVENTION

The present invention provides a self adjusting hydrocephalus valve that continuously drains cerebrospinal fluid in a patient at a rate which is proportional to the average pressure difference across the valve over time. In addition, the valve has an associated valve mechanism including a resistor, which is insensitive to high frequency pressure variations, for regulating the opening pressure of the valve mechanism. The valve of the present invention can be incorporated into a shunt device 10 similar to the one shown in FIG. 1 which employs a ball-in-cone mechanism 20 as described, for example, in U.S. Pat. Nos. 3,886,948, 4,332,255, 4,387,715, 4,551,128, 4,595,390, 4,615,691, 4,772,257, and 5,928,182, all of which are hereby incorporated by reference. As shown in FIG. 2A, the ball-in-cone mechanism 20 includes a ruby ball which rests on a seat that is in fluid communication with CSF entering the shunt device. A spring exerts a resistance or spring force on the ruby ball so as to keep the ball on the seat. When the CSF force overcomes the spring force, the ruby ball is displaced and moves out of the seat so that CSF can exit the shunt device 10. The countervailing forces acting on the ruby ball are represented by the arrows shown in FIG. 2B. As illustrated, the spring is attached to a spiral cam which allows the resistance or spring force to be adjusted by increasing or decreasing the height of the attached arm of the spring. The entire valve mechanism 20 can be attached to a base plate within the shunt device 10. It is contemplated that the self-adjusting valve of the present invention can either replace or supplement the spring and cam assembly of the ball-in-cone mechanism of FIG. 2A.

Figure 3:
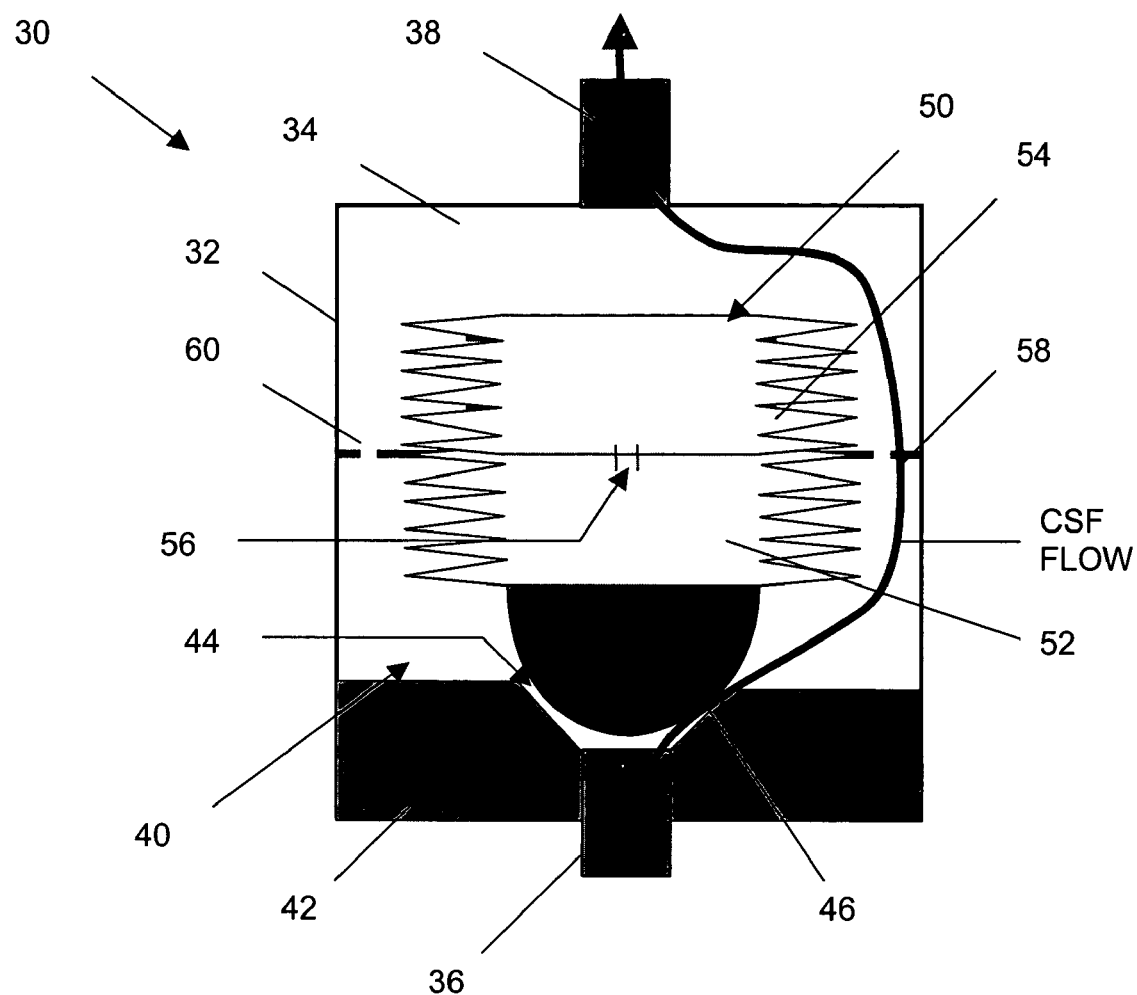
FIG. 3 is a cutaway view of a valve with an associated valve mechanism of the present invention.

Turning now to FIG. 3 in which an exemplary embodiment of the present invention is shown, the self adjusting valve 30 comprises a housing 32 enclosing a chamber 34 for fluid flow through the valve 30. Chamber 34 is in fluid communication with an inlet port 36 to accommodate the passage of CSF entering the valve 30 into the chamber 34 and an outlet port 38 to accommodate the passage of CSF out of the chamber 34.

To regulate the rate of fluid flow through the chamber 34, a valve mechanism 40 is disposed within the housing 32. The valve mechanism 40 includes a valve seat 44 formed on a base plate 42 within the housing 32. The valve seat 44 is adjacent to an opening in the inlet port 36 so that CSF can pass into the chamber 34. The valve seat 44 is configured to receive a blocking member 46 which, when seated against the valve seat 44, prevents fluid flow through the valve seat 44 and into the chamber 34. As shown in FIG. 3, the blocking member 46 can be a spherical ball, while the valve seat 44 can be configured with a contoured surface for mating with a portion of an outer surface of the spherical ball 46. However, it is contemplated that the valve seat 44 and blocking member 46 can have any complementary shape suitable for regulating fluid flow in and out of the valve 10.

The valve mechanism 40 also includes a biasing element 50 which communicates with the blocking member 46, acting as a shock absorber or damper, to bias the blocking member 46 against the valve seat 44. The biasing element 50 is configured to respond to a pressure difference within the valve 30, and has an adjustable resistance to allow fluid release at a rate which is proportional to an average pressure difference over time. The biasing element 50 can comprise any number of configurations, such as a spring, a collapsible membrane, and/or a flexible bellows. As illustrated in FIG. 3, the biasing element comprises a first flexible bellows 52 and a second flexible bellows 54. Each of the bellows 52, 54 can be cylindrically shaped. However, it is understood that the bellows 52, 54 can also have other shapes without departing from the spirit of the invention. The first flexible bellows 52 is connected in parallel to the second flexible bellows 54 by an orifice 56 which establishes a preset tension on the bellows 52, 54. The orifice 56, which is located between the two bellows, allows fluid communication between the first and second flexible bellows 52, 54. The orifice 56 can be substantially circular in shape, or it can be of alternative suitable shapes. The biasing element 50 is a closed fluidic system, i.e., the volume of fluid within the biasing element 50 stays constant. The first and second bellows 52, 54 can be filled with a fluid such as air, an inert gas, e.g., argon, nitrogen, or an oil, e.g., silicone oil. However, other suitable fluids can also be utilized.

A rigid support member 58 extends between the first and second bellows 52, 54 in the plane of the orifice 56. The support member 58 brackets or secures the biasing element 50 to the housing 32. The support member 58 is configured to provide sufficient rigidity to support the first flexible bellows 52 during collapse, without deflecting due to the pressure exerted against the support member 58 by the first flexible bellows 52. Support member 58 includes a plurality of openings 60 to enable fluid within the chamber 34 to pass around the biasing element 50. For example, the support member 58 can be perforated or include a plurality of apertures such as holes or slits to allow CSF fluid to flow through the support member 58.

As shown in FIG. 3, the first flexible bellows 52 is connected to the blocking member 46. The bellows 52 can rest on top of the blocking member 46, or the bellows 52 can be attached to the blocking member 46.

It is contemplated that the bellows 52, 54 can be formed of any material suitable for forming a collapsible and expandable structure which is impermeable to the fluids which it encloses, and the fluids surrounding the bellows 52, 54. Each of the bellows 52, 54 is formed of a conformable membrane. The conformable membrane can be a biocompatible, elastomeric material. The elastomeric material can be a polymer, such as thermoplastic material or polyurethane. Other suitable biocompatible polymeric materials also include polyethylene. The conformable membrane can also be formed of metal. Suitable metals include titanium, titanium alloy or titanium coated metal.

In operation, the biasing element 50 is configured to respond to a pressure difference within the valve 10, and to act as a damper or shock absorber to allow CSF release at a rate which is proportional to an average pressure difference over time. When CSF force acts on the blocking member 46 to unseat it, i.e., to lift it away from the valve seat 44 as illustrated in FIG. 3, the biasing element 50 adjusts according to the pressure exerted on the blocking member 46 by the CSF. For the blocking member 46 to rise, the first flexible bellows 52 has to decrease in volume, i.e., collapse, so that the blocking member 46 can rise up and allow fluid to flow through the valve seat 44 as the first flexible bellows 52 is compressed. The second flexible bellows 54 will necessarily increase in volume, i.e., expand, to compensate for the change to the first flexible bellows 52, since the biasing element 50 is a closed system and has a fixed total volume. As the first flexible bellows 52 collapses, fluid within that bellows 52 will exit out of the orifice 56 and into the second flexible bellows 54 to cause the expansion in the bellows 54.

The size of the orifice 56 determines the rate at which this transfer of fluid takes place. Where the orifice 56 is small in diameter, relative to the planar surface area of the bellows 52, 54 containing the orifice 56, a relatively large resistance to fluid flow is created by the orifice 56. Hence, the dimensions of the orifice 56 affects the rate at which the first flexible bellows 52 collapses and thus a relatively small orifice 56 creates a delayed response to CSF pressure exerted on the blocking member 46. By designing the valve mechanism 40 in this manner, the pressure drop created across the valve seat 44 limits the rate at which the blocking member 46 can lift. This creates a lag between the pressure wave and the associated opening of the valve 30. Hence, the preset tension on the bellows 52, 54 determines the desired average pressure across the valve 30, while the properties of the fluid in the bellows 52, 54, in combination with the size of the orifice 56, determines the average time required to drain CSF from the valve 30.

The valve mechanism 40 of the present invention can further be explained by the following equation:

$$X(t) = \text{EXP}(-t/\tau)\{\int \text{EXP}(t/\tau)*[P_{icp} - P_p] + \text{Const}\}$$

in which X(t) represents the translation, or vertical displacement, of the blocking member 46, $\tau$ is the system time constant, $P_{icp}$ is the fluid pressure upstream, and $P_p$ is the fluid pressure downstream of the valve 10. The above relationship shows that the blocking member 46 displacement X(t) is proportional to the average difference between the intracranial pressure ($P_{icp}$) and the pressure ($P_p$) of the body cavity (e.g., peritoneum or right atrium) where fluid is to be drained. The frequency response of the valve mechanism 40 is determined by the ratio of the bellows stiffness ($K_s$), the bellows area ($A_s$) and the orifice 56 resistance ($R_o$), where $A_s$ represents the average cross-sectional area of the bellows 52, 54, which are cylindrically shaped. Using this equation, the resistance $R_o$ of the orifice can be calculated for a given valve system, and its diameter or dimensions determined.

The time constant $\tau$ can be shown to be:

$$\tau = R_o A_s^2 / K_s$$

Figure 5:
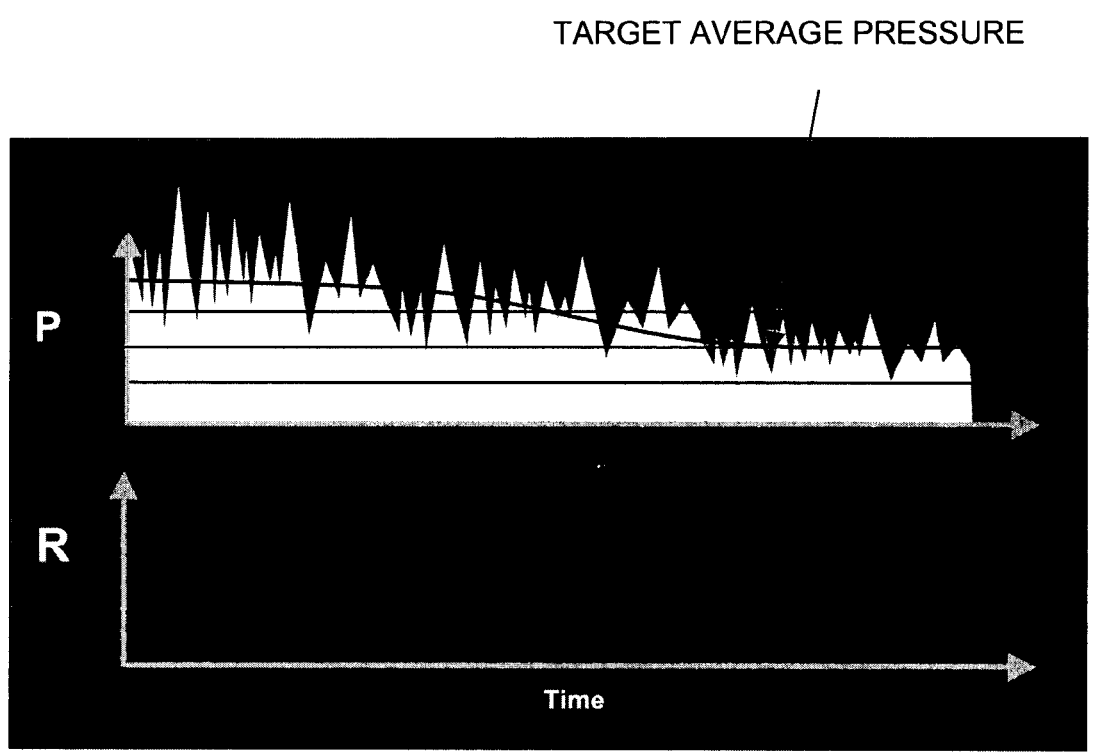
FIG. 5 is a graphical representation of the expected performance of the valve mechanism of FIGS. 3 and 4 over time.

The resistance of the valve 30 will be proportional to $X^2(t)$. The expected pressure time relationship of valve 30 of the present invention can be described in FIG. 5. As shown, the resistance of the valve 30 responds to changes in intracranial pressure. When the average pressure is high, the valve resistance is low. The low resistance causes the drainage rate to increase, thereby reducing the intracranial pressure. As the average intracranial pressure is lowered, the resistance increases and the average intracranial pressure reaches its predetermined level. It should be understood that, although the average intracranial pressure is controlled, significant variations in the instantaneous intracranial pressure still occur, thereby restoring the shunted patient's intracranial pressure to normal physiological levels and patterns. That is, because the pressure is allowed to instantaneously change, normal physiologic pressure waveforms are restored. It is further contemplated that the use of such a valve 30 would eliminate the need for a separate anti-siphon device.

Figure 4:
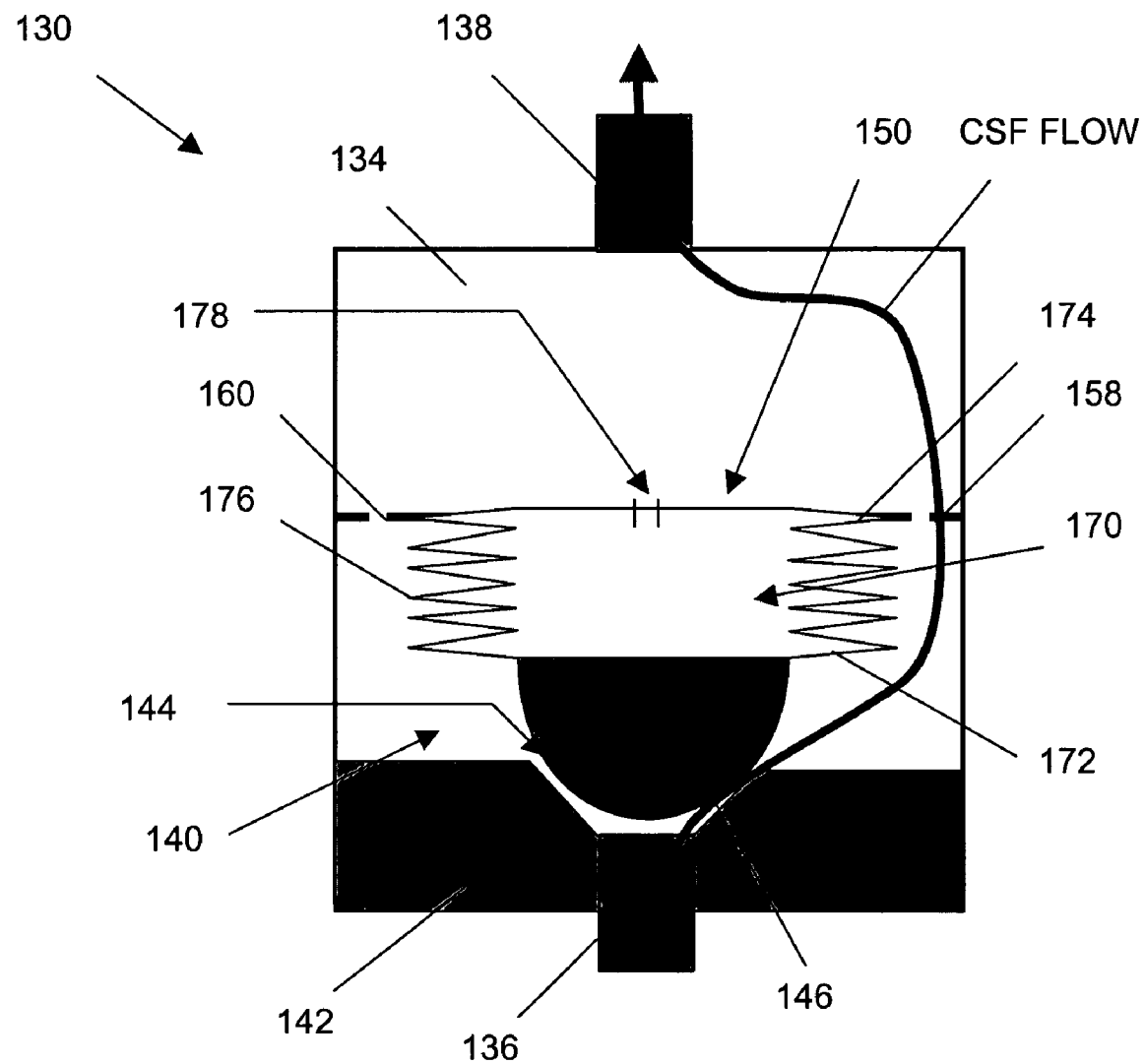
FIG. 4 is a cutaway view of another embodiment of a valve with an associated valve mechanism of the present invention.

The principles underlying the valve mechanism 40 of FIG. 3 can equally be applied to a biasing element which has a single flexible bellows. FIG. 4 illustrates another exemplary embodiment of the present invention, in which valve 130 shares similar features of valve 30 (all similar elements being designated by the same numeral following the prefix "1") except that the biasing element 150 contains a single bellows 170. Flexible bellows 170 is defined by a base plate 172, an opposed end plate 174, and a collapsible side wall 176 extending therebetween. The base plate 172 communicates with the blocking member 146, and can rest against or be directly attached to the blocking member 146. The opposed end plate 174 is connected to the support member 158. The plates 172, 174 can be round so that the flexible bellows 170 has a cylindrical shape. The flexible bellows 170 is an open fluidic system, and on the end plate 174 is an orifice 178 to provide fluid communication between the flexible bellows 170 and the chamber 134. The orifice 178, which allows fluid to pass into and out of the flexible bellows 170 and into the chamber 134, can be substantially circular in shape, or it can be of any other suitable shape.

As in the previous embodiment, the flexible bellows 170 is formed of a conformable membrane. It is contemplated that the conformable membrane can comprise any suitable material for forming a collapsible and expandable structure which is impermeable to the fluids which it encloses, and the fluids surrounding the bellows 170. The conformable membrane can be a biocompatible, elastomeric material. The elastomeric material can be a polymer, such as thermoplastic material or polyurethane. Other suitable biocompatible polymeric materials also include polyethylene. The conformable membrane can also be formed of metal. Suitable metals include titanium, titanium alloy or titanium coated metal.

The biasing element 150 is configured to operate in the same manner as biasing element 50. When CSF force acts on the blocking member 146 to unseat it, the biasing element 150 adjusts its volume according to the pressure exerted on the blocking member 146 by the CSF. For the blocking member 136 to rise, the flexible bellows 170 has to decrease in volume, i.e., collapse. As the flexible bellows 170 collapses, fluid within that bellows 170 will exit out of the orifice 178 and into chamber 134. The size of the orifice 178 determines the rate at which this transfer of fluid takes place. Where there is a relatively small orifice 178, the rate at which the flexible bellows 170 collapses is impeded by the resistance at the orifice 178 to fluid flow, and thus creates a delayed response to CSF pressure exerted on the blocking member 146. When the CSF pressure on the blocking member 146 decreases, the flexible bellows 170 collapses, and the blocking member 146 once again becomes seated in the valve seat 144. As the bellows 170 collapses, CSF fluid will enter the bellows 170 through the orifice 178 until a sufficient volume has been achieved to allow the bellows 170 to exert a force on the blocking member 146 sufficient to close the valve seat 144 and prevent or limit fluid entry.

Figure 1:
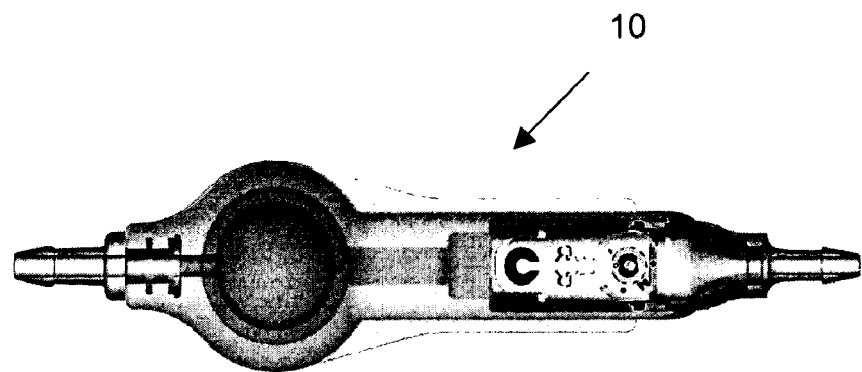
FIG. 1 is a top-down view of a shunt device enclosing a ball-in-cone valve mechanism of the prior art.
Figure 2A:
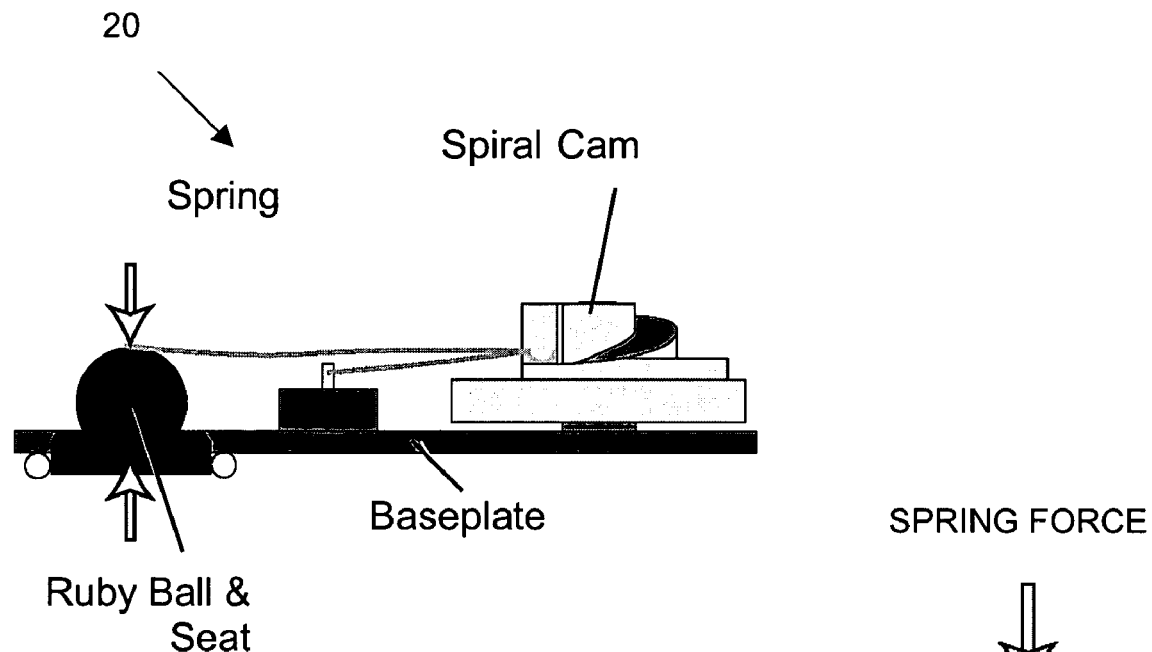
FIG. 2A is an enlarged side view of the ball-in-cone valve mechanism of the shunt device of FIG. 1.
Figure 2B:
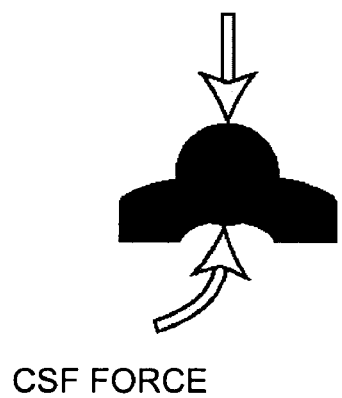
FIG. 2B is a more detailed side view of the ball-in-cone valve mechanism of FIG. 2A.

The valves 130, 30 of the present invention can be incorporated into a shunt device such as the device 10 shown in FIG. 1. It is contemplated that the self-adjusting valves 130, 30 of the present invention can either replace or supplement the spring and cam assembly of the ball-in-cone mechanism shown in FIG. 2A. That is, the biasing elements 50, 150 of the present invention can be placed between the ruby ball and the spring of the ball-in-cone mechanism of the prior art if desired.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A self adjusting hydrocephalus valve for regulating cerebrospinal fluid in a patient, comprising:
    a housing enclosing therein a chamber that is able to permit fluid flow therethrough,
    an inlet port in fluid communication with the chamber to accommodate passage of fluid into the chamber, and an outlet port in fluid communication with the chamber to accommodate passage of fluid out of the chamber; and
    a valve mechanism disposed within the housing for regulating the rate of fluid flow through the chamber, the valve mechanism including a valve seat adjacent to an opening in the inlet port, a blocking member configured to seat in the valve seat, and a biasing element for exerting a biasing force against the blocking member to selectively maintain the blocking member against the valve seat and prevent fluid flow therethrough, the biasing element being configured to respond to a pressure difference within the valve;
    wherein the biasing element has a self-adjusting, damped resistance to allow fluid release at a rate which is proportional to an average pressure difference over time, the biasing element configured to accommodate passage of fluid from the inlet port to the chamber without passage through the biasing element.

2. The valve of claim 1, wherein the biasing element is connected to the blocking member.

3. The valve of claim 1, wherein the biasing element comprises a spring element.

4. The valve of claim 1, wherein the biasing element comprises at least one flexible bellows defined by a base plate, an opposed end plate, and a collapsible side wall extending therebetween.

5. The valve of claim 4, wherein the biasing element comprises a single flexible bellows.

6. The valve of claim 5, wherein the end plate connects to a support member for securing the biasing element to the housing.

7. The valve of claim 5, wherein the support member includes apertures permitting fluid flow therethrough.

8. The valve of claim 5, wherein the end plate of the single flexible bellows includes an orifice to provide fluid communication between the single flexible bellows and the chamber.

9. The valve of claim 4, wherein the at least one flexible bellows is formed from a biocompatible elastomeric material.

10. The valve of claim 4, wherein the biasing element comprises two flexible bellows, the first flexible bellows being sequentially connected to the second flexible bellows.

11. The valve of claim 10, wherein the first and second bellows are connected by an orifice such that the first flexible bellows is in fluid communication with the second flexible bellows.

12. The valve of claim 11, further including a support member extending between the first and second flexible bellows for securing the biasing element to the housing.

13. The valve of claim 12, wherein the support member includes apertures permitting fluid flow therethrough.

14. The valve of claim 13, wherein the first flexible bellows is connected to the blocking member.

15. The valve of claim 13, wherein the first and second flexible bellows are formed from a biocompatible elastomeric material.

16. The valve of claim 13, wherein the biasing element is at least partially filled with a fluid.

17. The valve of claim 16, wherein the fluid is an inert gas.

18. The valve of claim 10, wherein the first and second bellows form a closed fluidic system.

19. The valve of claim 1, wherein the blocking member is a spherical ball.

20. The valve of claim 19, wherein the valve seat has a spherical surface for mating with a portion of an outer surface of the spherical ball.

* * * * *